(12) United States Patent  
Moine (10) Patent No.: US 8,110,238 B2
(45) Date of Patent: Feb. 7, 2012

(54) DRINK-TREATMENT METHOD WHICH IS USED TO INCREASE THE SWEETNESS THEREOF AND COMPOUND TO BE ADDED TO A DRINK IN ORDER TO INCREASE THE SWEETNESS OF SAME

(75) Inventor: Virginie Moine, Bordeaux (FR)

(73) Assignee: Sarco, Floirac (FR)

( * ) Notice: Subject to any disclaimer, the term of this patent is extended or adjusted under 35 U.S.C. 154(b) by 804 days.

(21) Appl. No.: 11/720,399

(22) PCT Filed: Nov. 28, 2005

(86) PCT No.: PCT/FR2005/050998
§ 371 (c)(1),
(2), (4) Date: Jun. 17, 2008

(87) PCT Pub. No.: WO2006/056725
PCT Pub. Date: Jun. 1, 2006

(65) Prior Publication Data
US 2009/0252847 A1    Oct. 8, 2009

(30) Foreign Application Priority Data
Nov. 29, 2004   (FR) ...................................... 04 52803

(51) Int. Cl.
*A23L 1/236* (2006.01)
(52) U.S. Cl. ...................... 426/546; 530/300; 435/255.1

(58) Field of Classification Search .................. 426/548; 530/300; 435/255.1
See application file for complete search history.

(56) References Cited

U.S. PATENT DOCUMENTS
2004/0101934 A1    5/2004   Choe et al.

FOREIGN PATENT DOCUMENTS
EP    0 418 616 A2    3/1991
WO    0146380 A1    6/2001

OTHER PUBLICATIONS

SU 657061—English Abstract.pp. 3-4.*
Martinez-Rodriquez, A. J. et al. 2000. Characterization of the nitrogen compounds released during yeast autolysis in a model wine systme. J. Agric. Food Chem. 48:1081-1085.*
Bernard F. Gibbs, et al., "Sweet and Taste-Modifying Proteins: A Review", Nutrition Research, vol. 16, No. 9, pp. 1619-1630, 1996.

* cited by examiner

*Primary Examiner* — D Lawrence Tarazano
*Assistant Examiner* — Hamid R Badr
(74) *Attorney, Agent, or Firm* — Perman & Green, LLP (57) ABSTRACT

The disclosed embodiments concern a processing method for a beverage destined for human or animal consumption with the aim of increasing the sweetness of said beverage, characterized in that a yeast preparation inerted by enzymatic and/or physical-chemical treatment containing a peptide sweetener with a molecular weight equal to 2.750+/−0.1 kDa is added to the beverage. The disclosed embodiments also concern such a sweetener compound.

11 Claims, 4 Drawing Sheets

DRINK-TREATMENT METHOD WHICH IS USED TO INCREASE THE SWEETNESS THEREOF AND COMPOUND TO BE ADDED TO A DRINK IN ORDER TO INCREASE THE SWEETNESS OF SAME

CROSS REFERENCE TO RELATED APPLICATIONS

This application is the National Stage of International Application No. PCT/FR2005,050998, International Filing Date, 28 Nov. 2005, which designated the United States of America, and which international application was published under PCT Article 21(2) as WO Publication No. WO 2006/056725 and which claims priority from German Application No. 0452803, filed 29 Nov. 2004.

BACKGROUND

1. Field

The disclosed embodiments relate to a method for processing a beverage, destined for human or animal consumption, with the aim of increasing the sweetness of said beverage. The method can be used for processing alcoholic beverages and for processing non-alcoholic beverages. The disclosed embodiments method can particularly apply to processing wine. A further aspect of the disclosed embodiments is a sweetener destined to be used for processing a beverage with the aim of increasing its sweetness.

2. Brief Description of Related Developments

Taste-modifying agents of different chemical and biological origins commonly used in the agri-foodstuff industry are well known, particularly for giving organoleptic characteristics to beverages and foodstuffs. For example, aspartame is a sweetening agent of peptide origin used in the agri-foodstuff industry. Proteins, such as thaumatin, can also possess sweetening properties of this kind (Gibbs et al., 1996).

Certain peptides probably of yeast origin (Desportes et al., 2001) and found in champagne-based wines are also cited as possessing organoleptic properties such as bitterness, acidity and umami (beef stock flavour).

However, these peptides often need to be added in large doses to beverages in order to be detected on a sensory level. The term "large dose of peptide", as used herein, is understood to mean at least 5 g/L.

In the regulatory context of oenological practices, certain processes are allowed in order to improve the organoleptic properties of wines, and one of these is ageing on lees.

During ageing on lees, a great number of biochemical and physical-chemical phenomena take place in the wine, which tend to modify its organoleptic properties.

Ageing white wines on lees is a very old technique used in maturing "grands vins" white wines in vats, particularly those from the Burgundy region. This method of maturing is now used all over the world. The biochemical and physical-chemical phenomena associated with this practice are the results of interactions between the wine, the yeasts and possibly with the wood, and lead to the improvement of the organoleptic qualities and the physical-chemical stability of the white wines stored in this way.

For example, the lees modify the woody flavour of white wines. Particularly, the vanilla flavour is less intense in wines that are fermented and stored in barrels than when they are run off after alcoholic fermentation and/or stored decanted. This phenomenon is due to the reduction of vanillin by the yeasts contained in the lees (Chatonnet et al., 1992). On the other hand, the fermentation and storage in barrels may also increase the toasted flavours, by the production of furan-methanethiol by the lees from the furfural in the heated wood (Tominaga et al., 2000).

Ageing on lees also increases the parietal polysaccharide content of the wines, and particularly the mannoprotein content (Llaubères et al., 1987). The result is a spontaneous improvement of the protein (Ledoux et al., 1992) and tartaric (Moine-Ledoux et al., 1997) stability of the wines. Moreover, the polysaccharides liberated during the ageing on lees can combine with the phenol compounds of the wine and the ellagitanins from the barrel (Chatonnet et al., 1992). This natural clarifying carried out during the batonnage (stirring) of the lees helps stop the colour of white wine changing and also helps stop the wood tannin bitterness developing and prevents the wine from pinking on oxidation.

Moreover, thanks to their reducing power, lees play a key part in reduction-oxidation phenomena. Fornairon et al., 1999, have recently shown their capacity to bind dissolved oxygen. In barrels their presence is absolutely necessary to protect certain fruity aromas from oxidation.

At the same time, lees prevent the oxidative aromas characteristic of defective aromatic ageing from developing (Lavigne-Cruège et al., 1999). Storing wine on lees can lead to the appearance of unpleasant sulphur odours, so that the wine needs decanting rapidly. In fact, as long as the sulphite reductase remains in the yeasts, dry white wines undergoing vinification in large capacity vats cannot be aged on lees, without the risk of reduction defects appearing. But if the lees are temporarily separated from the wine and stored in barrels, they can be reintroduced later when they have lost all their reducing activity. Moreover, their addition at this stage brings about a very marked decrease in the concentration of certain thiols such as methanethiol or ethanethiol. Disulphide bridges exist between the cysteine residues that constitute these mannoproteins (located in the outer walls of the yeast cells) and the SH groups of the thiols, which allow the yeasts to fix the thiols (Lavigne et Dubourdieu, 1996).

The many positive consequences of ageing white wines on lees have led some winemakers to apply this practice to maturing red wines, hoping to obtain organoleptic advantages, since the lees are purported to make wines "fat and well rounded", that is, to make them sweeter.

In red wines, ageing on lees also helps limit oxidation phenomena while acting, to a certain extent, on the texture of the wines. It has been reported in the literature (Escot et al. 2001) that glycoproteins of parietal origin, released during the autolysis of the yeasts present in the lees, seem to have an action on certain polyphenolic fractions resulting in a decrease in the astringent sensations related to these fractions.

In general, as those skilled in the art are well aware, one of the several effects of ageing red or white wines on lees is an increase in the sweetness of said wines.

However, it is not easy for the practitioner to manage these increases in sweetness. This is because controlling the ageing on lees depends on many factors, such as the duration, the temperature, the frequency of batonnage, the colloid structure of the wine, etc.

Moreover, this technique is costly to implement, and so cannot be envisaged on all wines. Lastly, this technique generally only applies to alcoholic beverages.

SUMMARY

The aspects of the disclosed embodiments, seek to provide a processing method that can be applied to all types of beverage, whether alcoholic or not, which make it possible to increase the palatability of the beverage, and more specifically the sweetness, in a controlled manner. The expression "controlled manner", as used herein, is understood to mean in a manner that achieves the desired palatability, which can vary from one beverage to another, depending on the requirements of the consumers, standards, etc.

In order to do this, the disclosed embodiments describe the use of an inerted yeast preparation containing a particular peptide, with a molecular weight comprised between 0.5 and 3 kDa, so as to increase the sensation of sweetness of the beverage to which it is added. This inerted yeast preparation can be obtained by autolysis of the yeasts present in the wine lees, such as for example the yeasts belonging to the *Saccharomyces cerevisiae* species.

The use of the inerted yeast preparation containing the peptide concerned is of particularly interest for processing wines, whether whites, reds or roses. This is because, in this case, the addition of the inerted yeast preparation of the disclosed embodiments correspond to the addition of an oenological product authorised by legislation.

The use of this yeast preparation makes it possible to process all sorts of beverages for human or animal consumption in order to increase the sweet sensation perceived when the beverage is absorbed.

Obviously, it is possible to use the yeast preparation containing the peptide according to the disclosed embodiments to increase the sweetness, or more generally to improve the palatability, of all sorts of agri-foodstuffs. The yeast preparation of the disclosed embodiments can particularly be used in the preparation of prepared food, milk-based foodstuffs or any other product destined for the retail market. The yeast preparation according to the disclosed embodiments containing the taste-modifying peptide fraction concerned can also be used as a table sweetener in the same way as aspartame or other sweeteners currently in use.

In the case of beverages or foodstuffs for which the regulatory context authorises it, the taste-modifying peptide fraction according to the disclosed embodiments, obtained by chemical synthesis for example, can be added directly.

The taste-modifying peptide fraction according to the disclosed embodiments has a very low perception threshold compared to flavouring agents currently used in the agri-food industry. The term "perception threshold" as used herein, is understood to mean the minimum concentration of that peptide fraction necessary for consumers to detect it. Thus, thanks to its sweetening power, it is possible to add small quantities of the inerted yeast preparation containing said peptide fraction to a foodstuff or a beverage to obtain a desired increase in sweetness.

It is also possible to use the sweetening peptide fraction directly, previously isolated from the inerted yeast preparation containing it or obtained by chemical synthesis.

Thus one aspect of the disclosed embodiments is a processing method for a beverage destined for human or animal consumption with the aim of increasing the sweetness of said beverage, characterised in that a yeast preparation inerted by enzymatic and/or physical-chemical treatment containing a peptide sweetener with a molecular weight comprised between 0.5 and 3 kDa is added to said beverage.

The term "yeast preparation", as used herein, is understood to mean the intracellular fraction and the fragments of cell walls of said yeasts.

The term "yeasts inerted by enzymatic and/or physical-chemical treatment" as used herein, is understood to mean yeasts that have undergone autolysis with or without exogenous enzymes. The exogenous enzymes are for example β-1-3 glucanases and/or β-1-6 glucanases and/or proteases. The yeasts can also be inerted by a physical-chemical process, such as acidic, basic or thermal treatment, these treatments being optionally added to the enzymatic treatment.

The term "peptide sweetener" as used herein, is understood to mean a peptide compound that can increase the sweetness of the solution to which it is added.

More specifically, the yeast preparation of the disclosed embodiments contains a peptide sweetener with a molecular weight equal to 2.750 kDa, +/−0.1 kDa.

The yeast preparation according to the disclosed embodiments can be added to the beverage in the form of a powder, in its dissolved form in solution or any other form.

The peptide sweetener concerned, present in the yeast preparation according to the disclosed embodiments, has a retention peak at 34 minutes on a Superdex Peptide HR 10/30 HPLC column.

The yeasts of the inerted yeast preparation are for example yeasts present in wine lees.

The yeasts belong for example to the *Saccharomyces cerevisiae* species.

The processing method according to the disclosed embodiments applies to any alcoholic beverages and to any non-alcoholic beverages, in which a sweet flavour or increased sweetness is required.

In a particular example of the implementation of the disclosed embodiments, at least 50 g+/−10 g of the inerted yeast preparation is added to the beverage per hectolitre of the beverage to be treated. Obviously, this concentration can be adapted, that is, it can be decreased or increased, for example depending on the type of beverage and/or those for whom the beverage is destined.

According to the disclosed embodiments, it is also possible to process a beverage destined for human or animal consumption with the aim of increasing the sweetness of said beverage, by adding to said beverage at least one sweetener with at least 60% similarity to one of the peptide sequences SEQ ID NO 1, SEQ ID NO 2, SEQ ID NO 3, SEQ ID NO 4, SEQ ID No 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

The term "sweetener" as used herein, is understood to mean a peptide compound that can increase the sweetness of the solution to which it is added.

The term "60% similarity" as used herein, is understood to mean that the sweetener has at least 60% of consecutive amino acids in common with the amino acids of the peptide sequence SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

It is possible to add a preparation comprising of a mixture of several sweeteners, each of which has at least 60% similarity to at least one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29

The sweetener according to the disclosed embodiments can be added to the beverage in the form of a powder, in its dissolved form in solution or any other form.

In an example of implementing the processing method of the disclosed embodiments, the sweetener has at least 70% similarity to one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29, more preferably 80%, still more preferably at least 90% and even more preferably 95% or most preferably 98% similarity to at least one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID N) 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

It is possible to add a preparation comprising of a mixture of several sweeteners, each of which has at least 60% similarity to at least one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29 and preferably at least 70%, more preferably 80%, still more preferably at least 90% and even more preferably 95% or most preferably 98% similarity to at least one of these sequences Another aspect of the disclosed embodiments is a peptide sweetener of yeast origin, characterised in that its molecular weight is comprised between 0.5 and 3 kDa.

More specifically, the peptide sweetener has a molecular weight equal to 2.750 kDa, +/−0.1 kDa.

The peptide sweetener according to the disclosed embodiments presents a perception threshold in a 12% hydroalcoholic solution of 16 mg/L +/−5 mg/L.

A further aspect of the disclosed embodiments is a peptide sweetener characterised in that it presents at least 60% of similarity to one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

The peptide sweetener can particularly be obtained by chemical synthesis or by extraction and purification from an inerted yeast preparation containing it.

In an particular example of producing the sweetener of the disclosed embodiments, said sweetener has at least 70% similarity to the peptide sequence SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29, more preferably 80%, still more preferably at least 90% and even more preferably 95% or most preferably 98% similarity to the peptide sequence SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

The peptide sweetener according to the disclosed embodiments can also be a homologue of a peptide with at least 60% similarity to the peptide sequence SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29, or a functional fragment of this peptide, or a chemical analogue of this peptide. The term "functional fragment of a peptide" as used herein, is understood to mean all sequences of at least two amino acids having a sweetening power. Another object of the invention is a preparation of yeasts inerted by enzymatic and/or physical-chemical treatment characterised in that it contains a peptide sweetener with a molecular weight comprised between 0.5 and 3 kDa.

The yeast preparation of the disclosed embodiments contains more specifically a peptide sweetener with a molecular weight of 2.750 kDa, +/−0.1 kDa.

Another aspect of the disclosed embodiments is a preparation of yeasts inerted by enzymatic and/or physical-chemical treatment characterised in that it contains a peptide sweetener with at least 70% similarity to the peptide sequence SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29, more preferably 80%, still more preferably at least 90% and even more preferably 95% or most preferably 98% similarity to at least one of the peptide sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29.

DESCRIPTION OF THE DRAWINGS

The following examples will show other advantages and characteristics, and will refer to drawings in the appendices wherein.

DESCRIPTION OF THE EMBODIMENTS

Identification of Taste-Modifying Fractions Liberated by Autolysis of Yeasts In order to identify the molecules with a sweetening property, or taste-modifying fraction, the inventors used yeasts present in wine lees in their work.

The term "autolysis", as used herein, is understood to mean the digestion of the materials that make up the yeasts by the action of endogenous enzymes, that is of enzymes belonging to said yeasts.

The identification of taste-modifying fractions released by autolysis of the yeasts is carried out on an autolysis model medium. The autolysis model medium is obtained from a synthetic medium subjected to alcoholic fermentation.

1.—Material 1.1.—Preparation of the Synthetic Medium

The composition of the synthetic medium is described in Table I.

TABLE I

| Composition of the synthetic medium | |
|---|---|
| | Concentration (g/l) |
| Glucose (VWR) | 100 |
| Fructose (VWR) | 100 |
| Tartaric acid (VWR) | 3 |
| Citric acid (VWR) | 0.3 |
| (L-)malic acid (Sigma) | 0.3 |
| Potassium phosphate (VWR) | 2 |
| Magnesium sulphate (VWR) | 0.2 |
| Ammonium sulphate (Sigma) | 0.3 = 63.6 mg N |
| Asparagine (Sigma) | 0.6 = 127.2 mg N |
| Meso-inositol (VWR) | 0.3 |

TABLE I-continued

| Composition of the synthetic medium | |
|---|---|
| Solution of oligo-elements concentrated 1000 times | Final concentration in mg/l |
| $MnSO_4$, 7 $H_2O$ (Sigma) | 4 |
| $ZnSO_4$, 7 $H_2O$ (Sigma) | 4 |
| $CuSO_4$, 5 $H_2O$ (Sigma) | 1 |
| KI (potassium iodide) (Sigma) | 1 |
| $CoCl$, 6 $H_2O$ (Sigma) | 0.4 |
| $(NH_4)_6Mo_7O_{24}$, 4 $H_2O$ (Sigma) | 1 |
| $H_3BO_3$ (boric acid) (Sigma) | 1 |
| Solution of vitamins concentrated 1000 times | Final concentration in mg/l |
| Biotine (Sigma) | 40 µg |
| Thiamine (Sigma) | 1 |
| Pyridoxine (Sigma) | 1 |
| Nicotinic acid (Sigma) | 1 |
| Pantothenic acid (Sigma) | 1 |
| Para-aminobenzoic acid (Sigma) | 1 |
| Solution of fatty acids concentrated 1000 times | Final concentration in mg/l |
| C 16 palmitic acid (Sigma) | 100 |
| C 16-1 palmitoleic acid (Sigma) | 20 |
| C 18 stearic acid (Sigma) | 300 |
| C 18-1 oleic acid (Sigma) | 50 |
| C 18-2 linoleic acid (Sigma) | 50 |
| C 18-3 linolenic acid (Sigma) | 20 |

All the glassware used during the preparation of this synthetic medium, and the filter system are autoclaved for 10 minutes at 105° C. prior to use.

In the first instance, the sugars, acids, nitrogen sources, potassium phosphate, magnesium sulphate, meso-initol and the solutions of vitamins and oligo-elements are dissolved in MilliQ water (Millipore). The pH is adjusted to 3.3, with 4N potassium hydroxide (VWR).

$SO_2$ is added at a concentration of 2 g/hl.

The mixture obtained is filtered in sterile conditions on a 0.45 µM cellulose ester membrane (Pall).

In parallel, the necessary volume of fatty acids is added to 0.5 g/l of cellulose (Granucell, Laffort OEnologie) then dissolved in 100 ml of ethanol.

This suspension is evaporated to dryness in a Rota-Vapor. The white powder obtained (cellulose onto which the fatty acids are fixed) is dissolved in the filtered synthetic medium. The turbidity of the medium is then 150 NTU.

1.2—Preparation of the Autolysis Medium

The synthetic medium is plated with 10 g/hl of *Saccharomyces cerevisiae* "Montrachet" strain 522 Davis (Active Dry Yeasts: Actiflore cerevisiae, Laffort OEnologie). The fermentation takes places in 6 litre round-bottom flasks. The yeasts are regularly oxygenated by rapid bubbling with compressed air. The concentration of residual reducing sugars at the end of fermentation is estimated by the "Clinitest" (Bayer) method.

After the alcoholic fermentation, the yeasts are resuspensed in the fermented synthetic medium, which is separated into two modalities, carried out in triplicate.

A first modality consists in an autolysis medium with no exogenous enzyme.

A second modality consists in an autolysis medium to which 5 g/hL of exogenous enzyme is added. The exogenous enzymes are a mixture of proteases and glucanases.

The autolysis takes place at 30° C., in the dark, for 6 months and the lees are put back into suspension weekly.

Sampling during autolysis was carried out after 11, 42, 88, 123 and 148 days of autolysis. The yeasts are separated from the medium par centrifuging (4500 g, 10 mn). The supernatant is then analysed.

2—Analytical Methods Used to Identify the Taste-Modifying Fractions During Autolysis 2.1—Measuring the Optical Densities of the Autolysis Products at 280 nm and 254 nm.

After dilution, the optical density of the autolysis supernatants is measured at 280 and 254 nm in quartz cells of 1 cm light path compared with distilled water.

2.2—Assay of Nitrogen Compounds

The assay of the nitrogen compounds in the autolysis supernatants is carried out by ninhydrin calorimetric analysis (Rosen, 1957).

2.3—Fractioning the Molecules According to Size

The lees are eliminated from the autolysis model mediums by centrifuging and the supernatants are subjected to three successive tangential ultrafiltrations on a Minitan™ (Millipore) module with cutoff thresholds of 10, 3 and 0.5 kDa, so that they can be fractioned.

The product to be filtered is forced into the tangential ultrafiltration module by a type 112 Beckman pump. The filtrations are carried out at laboratory temperature (23° C.). The retentates are dialysed at 500 Da (Spectra/Por® CE [cellulose ester]) to desalinate them and eliminate the smallest molecules, then, they are lyophilised and stored at −18° C.

2.4—Sensory Evaluation

In order to identify the taste-modifying fraction or fractions from the autolysis mediums, and to check them against molecular fractions from the lees, two taste tests are carried out in parallel.

Each taste test consists of a triangle test. The triangle test consists in presenting three coded samples to a subject. Two samples are identical and the third is different. The subject must detect the different sample. After statistical interpretation of the results, the significant differences are determined for thresholds of 5, 1 or 0.1%.

A first taste test compares the three molecular fractions, originating from the fractioning of purified lees, to a synthetic solution.

The synthetic solution is a hydroalcoholic solution comprised of 1.5 g/L of tartaric acid; 1.5 g/L of malic acid; 12% ethanol (v/v). The pH of the hydroalcoholic solution is 3.5 (by adding 1M NaOH). The hydroalcoholic solution is titrated at 12% v/v so as to mimic the percentage of alcohol in the wine.

A second taste test compares the different autolysis products, according to the autolysis medium, that is with or without exogenous enzyme.

2.5—Identification of the Perception Threshold of the Sweet Flavour.

The test for a perception or detection threshold of sweetness consists in presenting to a subject a sample having a given concentration of the sweetening component. The subject must then determine whether or not this sample is different from the control.

A mathematical model is associated to the variation of frequencies of response as a function of the concentration of the sweetener.

The perception threshold is defined as the concentration from which 50% of tasters systematically detect the presence of the substance.

The responses are obtained using a series of triangle tests.

A range of five concentrations of the sweetener for which the perception threshold is to be estimated is previously determined in a laboratory. This range of concentrations is then submitted to a jury of tasters. A triangle test is prepared for each of the concentrations to be tested. The samples are presented to the jury in order of increasing concentrations.

3—Results 3.1—Change in the Quantity of Substances Released During Autolysis.

Since the substances released during autolysis were mainly proteins or peptides and nucleic acids, their release into the medium was monitored by respectively measuring the change in the optical densities at 280 and 254 nm.

Figure 1A:
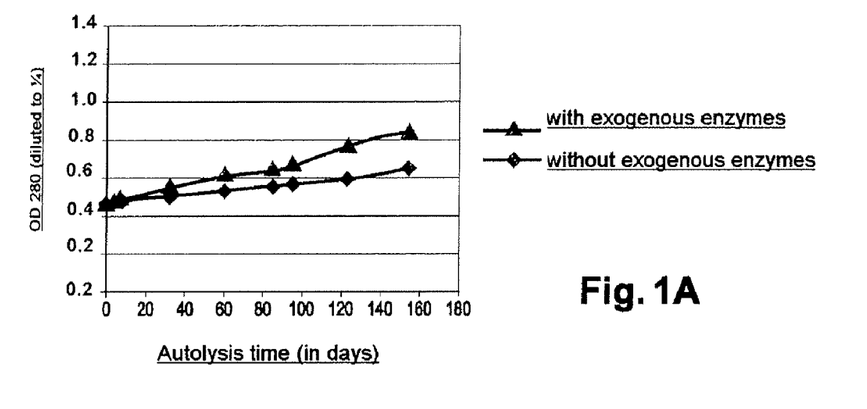
FIGS. 1A and 1B show the results of measures in the change of OD respectively at 254 nm (FIG. 1A) and at 280 nm (FIG. 1B) in a yeast autolysis medium whether or not the medium is enriched in exogenous enzymes.
Figure 1B:
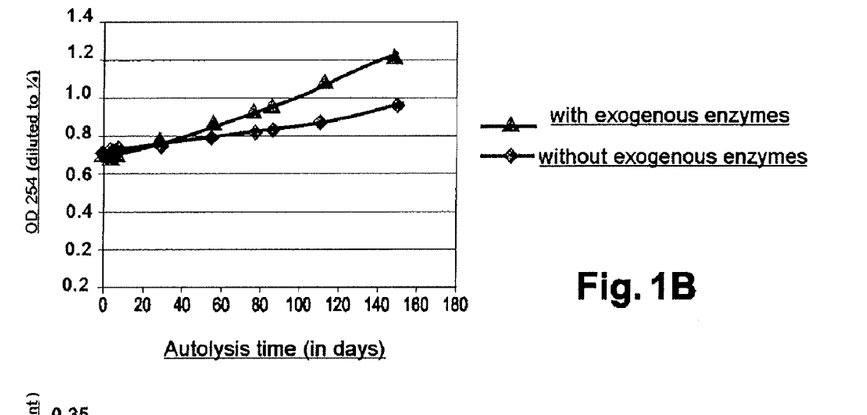

The results are given in FIGS. 1A and 1B.

By comparing the increase in the optical density in the autolysis medium without exogenous enzymes with the optical density in the autolysis medium with exogenous enzymes, a more rapid increase in OD is noted, whether it be at 254 nm or at 280 m, in the autolysis medium enriched in exogenous enzymes. This more rapid increase in OD in the autolysis medium enriched in exogenous enzymes becomes significant as from the third sample withdrawal that is to say, as from the $88^{th}$ day of autolysis.

The increase in optical densities at 280 and 254 nm is about 43% during the first sample withdrawal, compared to the optical density before autolysis, in the autolysis mediums treated with 5 g/hl of exogenous enzymes.

3.2—Change in Concentrations of Nitrogen Compounds

Figure 2:
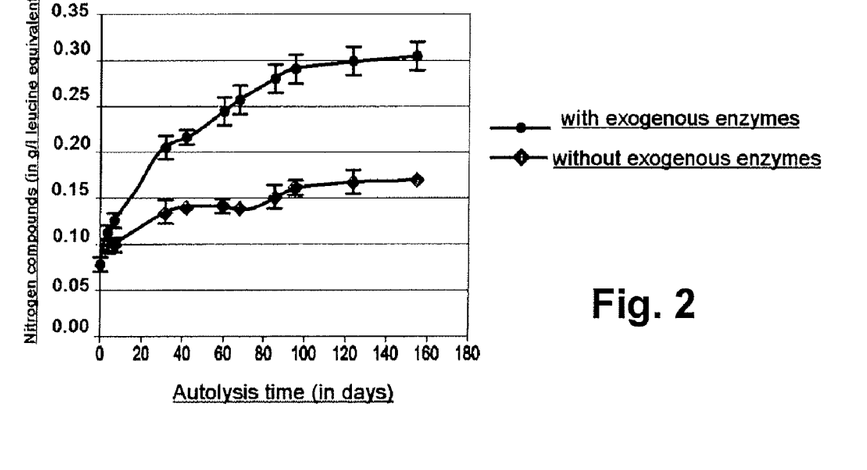
FIG. 2 shows the change in concentration, in g/l leucine equivalent, in nitrogen compounds in yeast autolysis medium whether or not the medium is enriched in exogenous enzymes.

The results of the assay of nitrogen compounds released during the autolysis, in presence or absence of exogenous enzymes is given in FIG. 2.

After 160 days of autolysis, the concentration in nitrogen compound is 0.3 g/L leucine equivalent in the autolysis medium enriched in exogenous enzymes compared with about 0.16 g/L leucine equivalent in the autolysis medium with no exogenous enzyme. Thus these results confirm those obtained during the measurement of the change in optical density.

Thus the presence of exogenous enzymes in the autolysis medium has a positive effect on the release of molecules of yeast origin into the autolysis medium. The term "positive effect", as used herein, is understood to mean that the molecules are released into the medium more rapidly and in greater quantities.

3.3—Results of Triangle Tests

The triangle tests were carried out in order to allow sensory evaluation of the molecular fractions released during the autolysis, in the presence or in the absence of enzymes.

To do this, fractioning was carried out respectively on the autolysis medium without exogenous enzyme and on the autolysis medium enriched in exogenous enzymes, after 154 days.

The concentrations of nitrogen compounds of these different fractions in the two mediums, at 154 days, are given in Table I below.

TABLE I concentrations of nitrogen compounds in the different fractions

|  | Autolysis medium without exogenous enzyme | | | Autolysis medium with exogenous enzymes | | |
| --- | --- | --- | --- | --- | --- | --- |
|  | Fractions | | | | | |
|  | >10 kDa | 3-10 kDa | 0.5-3 kDa | >10 kDa | 3-10 kDa | 0.5-3 kDa |
| Nitrogen compounds (mg/L) | 60 | 10 | 110 | 90 | 20 | 200 |

3.3.1—First Sensory Evaluation: Identification of the Taste-Modifying Fraction.

The first sensory evaluation is composed of three triangle tests comparing the purified fractions originating from the autolysis in the presence of enzymes, with the synthetic hydroalcoholic solution alone.

The results are given in Table II below.

TABLE II

Results of sensory analysis of three isolated molecular fractions compared with the synthetic hydroalcoholic solution alone.

| | Compared modalities | | |
|---|---|---|---|
| | Fraction 0.5-3 kDa | Fraction 3-10 kDa | Fraction >10 kDa |
| Number of tasters | 7 | 7 | 7 |
| % of correct answers | 100 | 43 | 14 |
| Significant difference | Yes (0.1% threshold) | No | No |

These tests show that only the fraction comprised between 0.5 and 3 kDa can be distinguished by taste from the synthetic solution by 100% of tasters, at a concentration of 200 mg/L.

The molecules larger than 10 kDa have no organoleptic function.

3.3.2—Second Sensory Evaluation: Detection Threshold of the Taste-Modifying Fraction Based on the results of the first sensory evaluation, the attempt was made to discover the threshold value for the detection of the taste-modifying fraction comprised between 0.5 and 3 kDa. The perception threshold of this taste-modifying fraction was sought by enriching the synthetic hydroalcoholic solution with increasing concentrations of the taste-modifying fraction concerned.

The results of this test are given in Table III.

1 means that the taster gave a correct answer in the triangle test;

0 means that the taster did not give a correct answer in the triangle test;

TABLE III

Results of triangle tests for determining the perception threshold of the taste-modifying fraction.

| Tasters | 2 mg/L | 4 mg/L | 8 mg/L | 16 mg/L | 32 mg/L |
|---|---|---|---|---|---|
| 1 | 1 | 1 | 1 | 1 | 1 |
| 2 | 0 | 0 | 0 | 0 | 1 |
| 3 | 1 | 0 | 1 | 1 | 1 |
| 4 | 0 | 1 | 0 | 1 | 1 |
| 5 | 0 | 0 | 0 | 0 | 1 |
| 6 | 0 | 0 | 1 | 1 | 1 |
| 7 | 1 | 0 | 0 | 0 | 1 |
| 8 | 0 | 0 | 1 | 0 | 0 |
| total | 3 | 2 | 4 | 4 | 7 |

The taste-modifying fraction was detected by 50% of the tasters starting from a concentration of 16 mg/L. A correct answer is only considered to be relevant if the tasters concerned continue thereafter, for increasing concentrations, to give correct answers. For a concentration of 32 mg/L, 70% of tasters detect the presence of the taste-modifying fraction. Thus the detection threshold is particularly low compared with state of the art taste-modifying molecules currently used in the agri-foodstuff domain.

3.3.3—Third Sensory Evaluation: Comparison of Organoleptic Properties of the Taste-Modifying Fraction Originating From the Autolysis Medium With no Exogenous Enzyme and of the Taste-Modifying Fraction Originating From the Autolysis Medium Enriched With Exogenous Enzymes.

After having shown that only one of the isolated fractions is taste-modifying, we tested to see whether the molecules originating from the fractioning between 0.5 and 3 kDa produced in the two autolysis mediums, with and without exogenous enzymes, have the same organoleptic properties.

In order to do this, a triangle test is carried out, comparing the two taste-modifying fractions. The results of this test are given in Table IV.

TABLE IV

Results of the triangle tests comparing the palatability of each of the two fractions originating respectively from the autolysis medium with exogenous enzyme and from the autolysis medium without exogenous enzyme.

| | |
|---|---|
| Taste-modifying fractions compared for the triangle test | 0.5-3 kDa fraction originating from the autolysis without exogenous enzyme/ 0.5-3 kDa fraction originating from the autolysis with exogenous enzymes |
| Number of tasters | 10 |
| % of correct answers | 30 |
| Significant difference | No |

The taste-modifying fractions originating from the two autolysis mediums cannot be differentiated from an organoleptic point of view. Thus they are equivalent.

Thanks to these successive tests, the palatability of the fraction with a molecular weight comprised between 0.5 and 3 kDa is demonstrated.

3.3.4—Fourth Sensory Evaluation: Confirmation of the Peptide Nature of the Fractions Concerned and of its Organoleptic Properties In order to confirm the peptide nature of the taste-modifying fraction, said fraction with a molecular weight comprised between 0.5 and 3 kDa is subjected to a non specific protease, proteinase K.

After hydrolysis, proteinase K is eliminated by ultrafiltration and the residual substances are recovered and dissolved in a synthetic hydroalcoholic solution.

A triangle test is carried out on this solution enriched with residual substances. The result of the triangle test is given in Table V below.

TABLE V

Result of the sensory analysis comparing a synthetic hydroalcoholic solution enriched with the molecular fraction with a molecular weight of 0.5-3 kDa after hydrolysis by proteinase K with a non enriched synthetic hydroalcoholic solution.

| | |
|---|---|
| Compared modalities | Synthetic hydroalcoholic solution enriched with 0.5-3 kDa molecular fraction after hydrolysis by proteinase K/non enriched synthetic hydroalcoholic solution. |
| Number of tasters | 13 |
| % of correct answers | 54 |
| Significant difference | No |

The results of this test show that there is no significant difference between the two solutions from an organoleptic point of view. This is because the statistical analysis of these results shows that at a 5% significance threshold, for 13 tasters, at least 61% of correct answers is needed for the difference to be considered as significant, because of the percentage of correct answers that are due to chance. In the same way, at a significance threshold of 1%, for 13 tasters, at least 69% of correct answers is needed, and at a significance threshold of 0.1%, for 13 tasters, at least 77% of correct answers.

This test makes it possible to confirm that the taste-modifying molecular fraction is of peptide origin, because it is digested by proteinase K.

This test also makes it possible to show that once the peptide compounds are hydrolysed, the 0.5-3 kDa fraction can no longer be differentiated. The taste-modifying fraction loses its organoleptic properties when it is hydrolysed.

Identification of the Presence of the Taste-Modifying Fraction Comprised Between 0.5-3 KDa in the Inerted Yeast Preparation Once the taste-modifying fraction has been identified and isolated, we attempted to check the presence of this taste-modifying fraction directly in the inerted yeast preparations. One of the aims was to know whether the peptide fraction concerned keeps its organoleptic properties when it is not isolated.

Identification of the Taste-Modifying Fraction in Inerted Yeast Preparations.

In order to identify the peptide fraction comprised between 0.5 and 3 kDa in the yeast extracts, a peptide analysis method for molecular screening by HPLC is used. An identical analysis is carried out in parallel on inerted yeast preparations and on the purified peptide fraction concerned.

The inerted yeast preparations and the purified taste-modifying fraction are separated according to their molecular weight on two types of columns, TSK G2000sw and Superdex Peptide HR 10/30, by high performance liquid chromatography (Spectrasytem AS 1000). The fractioning zone is from 10 to 70 kDa for the globular proteins for the first column and from 100 to 7000 Da for the second column.

The separation conditions are as follows:
TSK G2000sw
Injection volume 100 μl
Eluent NaCl 0.1 M
Flow rate: 0.6 ml/mn
SuperdexPeptide HR10/30
Injection volume 50 μl
Eluent 0.1 M
Flow rate 0.5 ml/mn
The detection is carried out in UV at 200 nm.

Figure 4A:
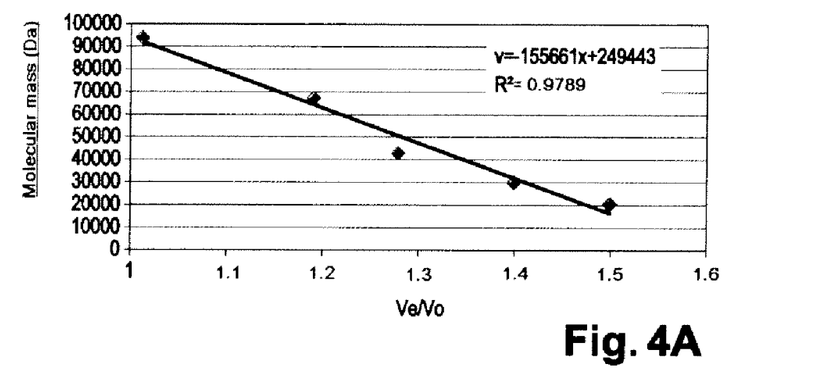
FIGS. 4A and 4B represent molecular calibrations respectively of a TSK S2000sw column (FIG. 4A) and a Superdex Peptide HR 10/30 column (FIG. 4B) for their use for separating peptides in a peptide preparation containing the taste-modifying fraction concerned and in an inerted yeast preparation.
Figure 4B:
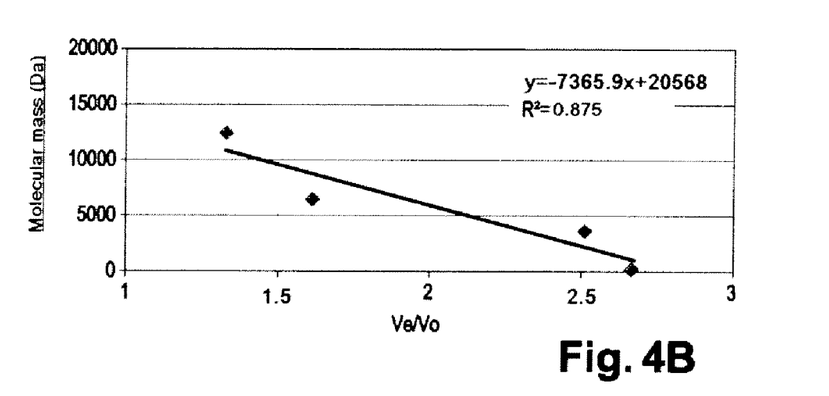

The calibration of the 2 columns is carried out with a mixture of proteins for different molecule sizes allowing a graph to be drawn for each column (see FIGS. 4A and 4B)

The molecular calibration of the TSK G2000sw (FIG. 4A) column is carried out as follows:
200000: blue dextran
94 500: phosphorylase B
67 000: bovine serum albumin
43 000: ovalbumin
30 000: carbonic anhydrase
12 500: cytochrome C The molecular calibration of the Superdex Peptide HR 10/30 (FIG. 4B) column is carried out as follows:
200000: blue dextran
12 500: cytochrome C
65000: Aprotinin
3500: insulin fragment
300: glutathion Results of Identification The identified taste-modifying fraction is analysed by HPLC following the two methods described above.

Figure 5A:
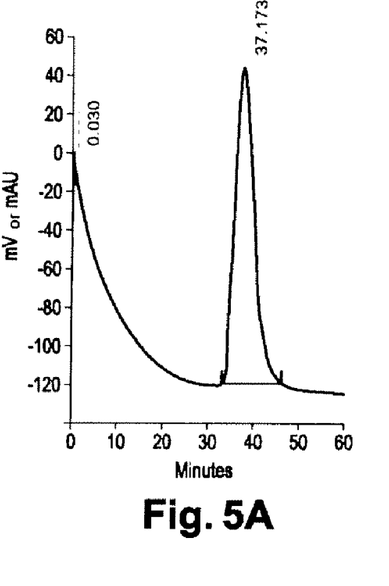
FIGS. 5A and 5B represent the chromatograms by high pressure liquid chromatography of the peptide preparation containing the taste-modifying fraction concerned respectively on TSK G2000sw (FIG. 5A) and on Superdex Peptide HR 10/30 (FIG. 5B)
Figure 5B:
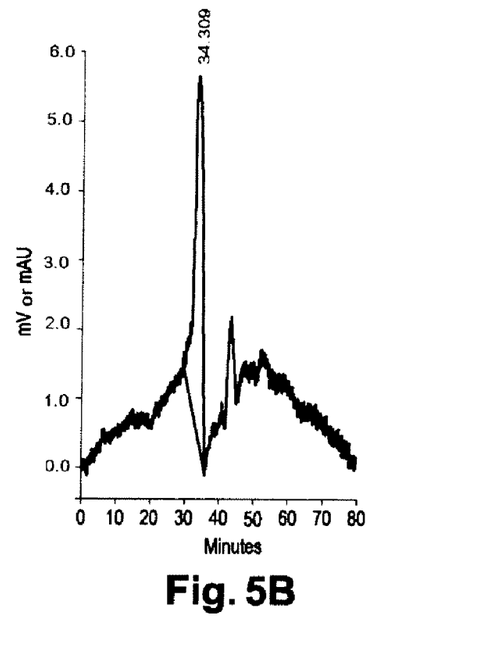

The FIGS. 5A and 5B show the results for the molecular screening by HPLC of the taste-modifying peptide fraction, purified respectively on TSK G2000sw (FIG. 5A) and on Superdex Peptide HT 10/30 (FIG. 5B).

The characteristic retention time of the purified taste-modifying peptide fraction is 37 minutes on the TSK G2000sw column and 34 minutes on the Superdex Peptide HR 10/30 column, corresponding to the molecular weight described previously, of under 3 kDa, that is about 2.750 kDa. The term "about 2.750 kDa" as used herein, is understood to mean 2.750 kDa plus or minus 0.1 kDa.

Figure 6A:
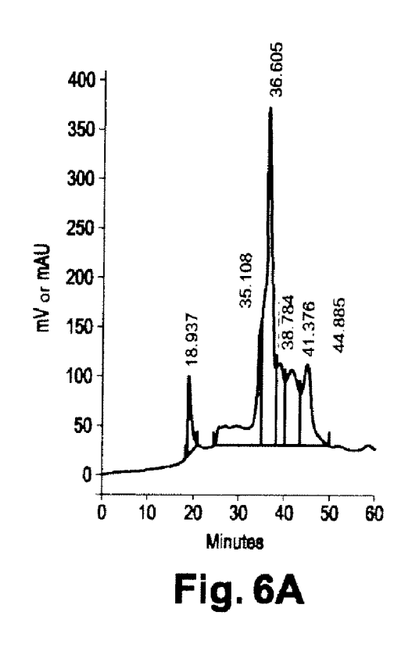
FIGS. 6A and 6B represent the chromatograms by high pressure liquid chromatography of an inerted yeast preparation respectively on TSK G2000sw (FIG. 5A) and on Superdex Peptide HR 10/30 (FIG. 5B)
Figure 6B:
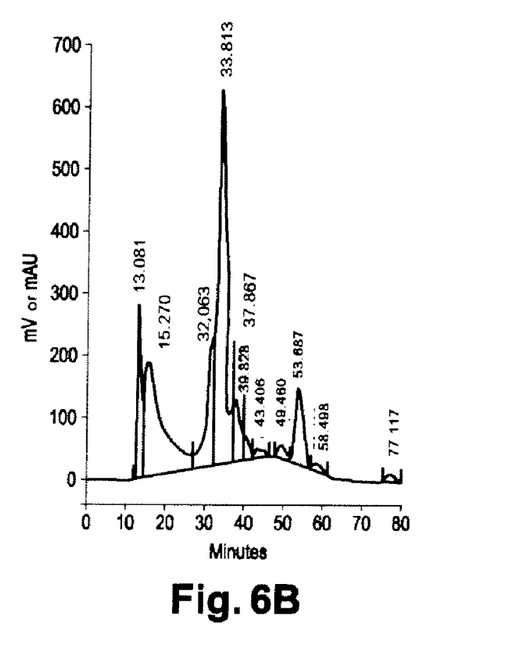

The different inerted yeast preparations are then analysed by HPLC. The comparison of one of the profiles obtained (FIGS. 6A and 6B) with that of the purified taste-modifying peptide fraction shows the presence, in all the types of yeast preparations analysed, of the fraction with the retention time of 37 minutes (FIG. 6A) and 34 minutes (FIG. 6B). The peptide corresponding to the retention time of 37 or 34 minutes in the yeast preparation has a molecular weight of about 2.750 kDa.

Thus, the presence in the taste-modifying peptide fraction is confirmed in the inerted yeast preparations.

The HPLC-based analysis methods make it possible to monitor the efficacy of the production of inerted yeast preparations. These analysis methods can be used systematically, as a quality control test of the inerted yeast preparations. The presence of a peak at the retention time of 34 minutes on the Superdex Peptide HR 10/30 column confirms the presence of the taste-modifying peptide fraction (2.750 kDa) in the preparation analysed.

Production of Inerted Yeast Preparation for Increasing the Sweetness of a Beverage.

We wanted to discover whether the quality of the organoleptic characteristics of the peptide fraction according to the invention could vary according to the yeasts used, and/or according to the processing to which the yeasts are subjected.

We made four different inerted yeast preparations. Preparations A, B, C and D correspond to the following processing:

Preparation A: yeasts of strain BO213 inerted by a physical-chemical method;

Preparation B: yeasts of strain 522D inerted by a physical-chemical method;

Preparation C: yeasts of strain 522D inerted by an enzymatic method;

Preparation D: yeasts of strain VL3C inerted by a physical-chemical method.

After production, the sensory impact of these different preparations is measured by triangle taste tests comparing wines to which these inerted yeast preparations have been added and the same untreated control wines. The jury of tasters is composed of 15 people.

Figure 3:
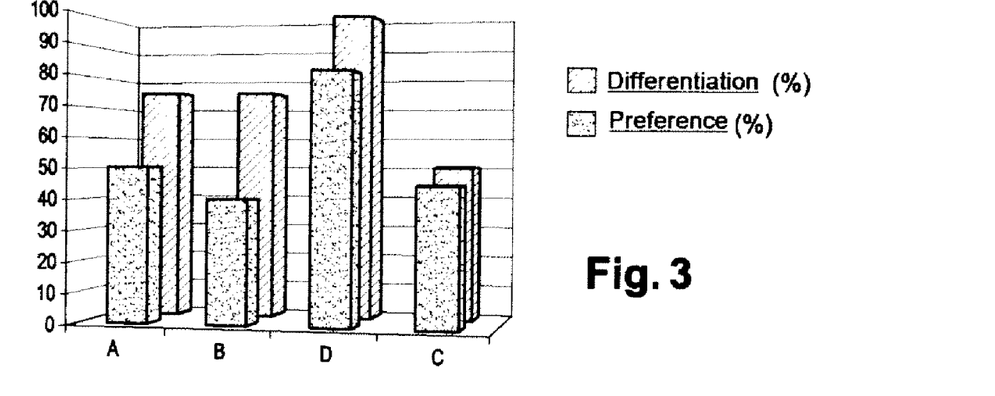
FIG. 3 shows the results of different triangle tests comparing the wines treated by adding different inerted yeast preparations to untreated wines.

An example of the results is described in FIG. 3.

The statistical analysis of these triangular taste tests shows that for the jury the significant differentiation threshold is reached as from 78% of correct answers. This threshold is only reached when the inerted yeasts of preparation D are added. In these conditions 100% of the tasters prefer the treated wine.

The sweetener peptide fraction is also present in the inerted yeast preparations A, B and C. However, the respective concentrations of sweetener peptide fraction in these preparations, is not sufficient to be detected by certain members of the jury.

These experiments show that the type of preparation of the inerted yeasts, by enzymatic treatment, physical-chemical treatment or thermal treatment, can have an influence on the presence of the sweetener peptide fraction that increases the palatability of wines. Depending on the treatment to which the yeast preparation is subjected, the inerted yeast preparation obtained has a greater or lesser concentration of sweetener peptide fraction.

Perception Threshold of the Inerted Yeast Preparation in Different Wines.

The preparation D of inerted yeasts was added to different types of wines in concentrations of 30, 50 and 70 g/hl. The sensory impact of these different treatments is measured by triangle taste tests comparing control wines to wines to which these inerted yeast preparations have been added. A jury of nine tasters participates in these triangle tests.

A statistical analysis is carried out in order to determine the significant answers. For a jury of nine tasters, a minimum of seven correct answers is needed, that is 78% of correct answers for the difference to be significant at a 5% threshold.

An example of these results is given in Table VI.

TABLE VI

Perception threshold of the inerted yeast preparation in different wines.

| Types of wines | 30 g/hL | | 50 g/hL | | 70 g/hL | |
|---|---|---|---|---|---|---|
| | Correct answers (%) | Significant difference | Correct answers (%) | Significant difference | Correct answers (%) | Significant difference |
| White wine Chardonnay 2003 | 56 | No | 78 | Yes | 78 | Yes |
| Red wine Cabernet Sauvignon 2003 | 45 | No | 56 | No | 78 | Yes |
| White wine Sauvignon 2003 | 78 | Yes | 78 | Yes | 78 | Yes |
| Red wine Merlot 2003 | 56 | No | 78 | Yes | 78 | Yes |
| Red wine Cabernet Sauvignon/ Merlot 2002 | 45 | No | 56 | Yes | 78 | Yes |

In all the examples in Table VI, except for the Cabernet Sauvignon 2003 red wine, the gustative quality of the wine is improved by adding 50 g/hl of inerted yeast preparation. The gustative quality of the Cabernet Sauvignon 2003 red wine is improved by adding 70 g/hl of inerted yeast preparation. The term "gustative quality" as used herein, is understood to mean an increase in sweetness.

Thus the palatability of the wine is increased by adding small quantities of inerted yeast preparations containing the taste-modifying fraction of the invention.

Purification and Sequencing of Peptides Contained in the Taste-Modifying Fraction The 0.5-3 kDa taste-modifying peptide fraction, originating from the inerted yeast preparations, is purified by high performance liquid chromatography (Spectrasystem AS 1000) molecular screening on a Superdex Peptide HR 10/30 column.

The taste-modifying peptide fraction eluted at 34 minutes retention time is collected.

Then the fraction is purified again by HPLC on a C18RP column in the following conditions:

Lichrospher RP18 5 µm 250×4.6 mm column

Eluent

Buffer A: Acetonitrile/Water (80/20);

Buffer B: Acetonitrile/Water (8/92)

| Gradient: | time (min) | % A | % B |
|---|---|---|---|
| | 0 | 15 | 85 |
| | 10 | 40 | 60 |
| | 15 | 81 | 19 |
| | 17 | 81 | 19 |
| | 18 | 81 | 19 |
| | 20 | 17 | 83 |
| | 22 | 17 | 83 |

Injection volume 100 µl

Flow rate 1 ml/mn

Detection 200 nm

Figure 7:
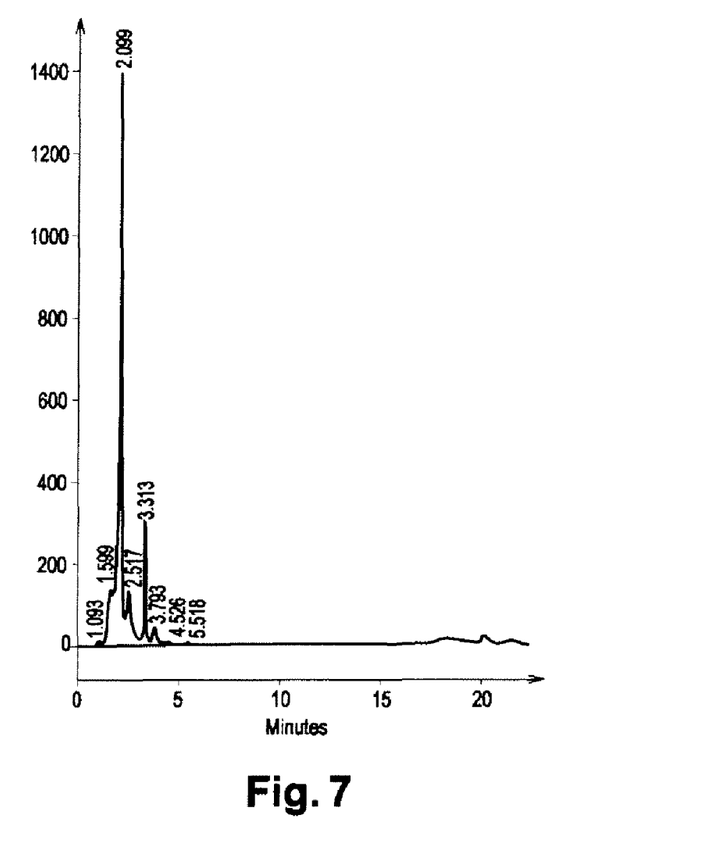
FIG. 7 represents the chromatogram by high pressure liquid chromatography of the taste-modifying fraction concerned on C18RP.

The taste-modifying fraction is eluted at 2.10+/−0.1 minutes retention time (FIG. 7).

About fifty injections are carried out and the taste-modifying fraction purified in this way is collected and assembled then evaporated in a vacuum and lyophilised.

The dry extract obtained is analysed by liquid chromatography coupled to a MS/MS mass detector.

A yeast library is then consulted in order to identify the proteins from which the isolated peptides originated.

The sequencing results show that the taste-modifying fraction contains twenty-nine peptides with the respective sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28 or SEQ ID NO 29, originating from nine *Saccharomyces cerevisiae* proteins.

More specifically, the nine identified proteins are, respectively a 12 kDa heat shock protein, for the peptides with the sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, and SEQ ID NO 11;

a Phosphoglycerate kinase (EC 2.7.2.3), for the peptides with the sequences SEQ ID NO 12, SEQ ID NO 13, SEQ ID NO 14, SEQ ID NO 15, and SEQ ID NO 16;

an Enolase 1 (EC 4.2.1.11) (2-phosphoglycerate dehydratase) (2-phospho-D-glycerase), for the peptides with the sequences SEQ ID NO 17, SEQ ID NO 18, SEQ ID NO 19, and SEQ ID NO 21;

a Phosphoglycerate mutase 1 (EC 5.4.2.1) (Phosphoglyceromutase 1) (PGAM 1) (MPGM) for the peptides with the sequences SEQ ID NO 20a, SEQ ID NO 22, and SEQ ID NO 23;

an elongation factor 1-alpha (EF-1-alpha), for the peptides with the sequences SEQ ID NO 24 et SEQ ID NO 25;

a Superoxide dismutase [Cu—Zn] (EC 1.15.1.1), for the peptide with the sequence SEQ ID NO 26;

a Rotenone-insensitive NADH-ubiquinone oxidoreductase mitochondrial precursor, for the peptide with the sequence SEQ ID NO 27;

a ribosomal protein 60S L26-A (YL33), for the peptide with the sequence SEQ ID NO 28;

the ORF YDL223c of chromosome IV, for the peptide with the sequence SEQ ID NO 29.

The peptide sweeteners of the taste-modifying fraction have at least 60% similarity to one of sequences SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, or SEQ ID NO 29.

These peptide compounds, isolated or in a mixture, have sweetening properties attributed to the taste-modifying fraction comprised between 0.5 and 3 kDa initially isolated from inerted yeast preparations and characterised by HPLC on TSK G2000sw with a retention time of 34 minutes or on Superdex Peptide HR 10/30 with a retention time of 34 minutes, according to the separation conditions described.

The invention claimed is:

1. A peptide sweetener of yeast origin, wherein said yeast is *Saccharomyces cerevisiae*, said peptide being obtainable by autolysis of yeast cells having a molecular weight of between 0.5 and 3 kDa and presenting at least 60% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

2. The peptide sweetener according to claim 1, having a molecular weight equal to 2.750 kDa, +/−0.1 kDa.

3. The peptide sweetener according to claim 1, having a perception threshold in a 12% hydroalcoholic solution of 16 mg/L+/−5 mg/L.

4. The peptide sweetener according to claim 1, presenting at least 70% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

5. The peptide sweetener according to claim 1, presenting at least 80% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

6. The peptide sweetener according to claim 1, presenting at least 90% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

7. The peptide sweetener according to claim 1, presenting at least 95% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

8. The peptide sweetener according to claim 1, presenting at least 98% similarity to one of the peptide sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11.

9. A method of using the peptide sweetener of claim 1 for processing a beverage destined for human or animal consumption with the aim of increasing the sweetness of said beverage, wherein said peptide sweetener is added to said beverage.

10. The processing method according to claim 9, wherein the peptide sweetener is added to an alcoholic beverage.

11. The processing method according to claim 9, wherein the peptide sweetener is added to a non-alcoholic beverage.

* * * * *

SEQUENCE LISTING

```
<160> NUMBER OF SEQ ID NOS: 29

<210> SEQ ID NO 1
<211> LENGTH: 16
<212> TYPE: PRT
<213> ORGANISM: Saccharomyces cerevisiae

<400> SEQUENCE: 1

Lys Ala Asp Lys Val Ala Gly Lys Val Gln Pro Glu Asp Asn Lys Gly
1               5                   10                  15

<210> SEQ ID NO 2
<211> LENGTH: 22
<212> TYPE: PRT
<213> ORGANISM: Saccharomyces cerevisiae

<400> SEQUENCE: 2

Lys Glu Tyr Ile Thr Asp Lys Ala Asp Lys Val Ala Gly Lys Val Gln
1               5                   10                  15

Pro Glu Asp Asn Lys Gly
            20

<210> SEQ ID NO 3
<211> LENGTH: 13
<212> TYPE: PRT
<213> ORGANISM: Saccharomyces cerevisiae

<400> SEQUENCE: 3

Lys Ala Ser Glu Ala Leu Lys Pro Asp Ser Gln Lys Ser
1               5                   10

<210> SEQ ID NO 4
<211> LENGTH: 16
<212> TYPE: PRT
<213> ORGANISM: Saccharomyces cerevisiae

<400> SEQUENCE: 4

Asp Ala Val Glu Tyr Val Ser Gly Arg Val His Gly Glu Glu Asp Pro
1               5                   10                  15

<210> SEQ ID NO 5
<211> LENGTH: 26
<212> TYPE: PRT
<213> ORGANISM: Saccharomyces cerevisiae
```

-continued

<400> SEQUENCE: 5

Lys Ala Ser Glu Ala Leu Lys Pro Asp Ser Gln Lys Ser Tyr Ala Glu
1               5                   10                  15

Gln Gly Lys Glu Tyr Ile Thr Asp Lys Ala
            20                  25

<210> SEQ ID NO 6
<211> LENGTH: 15
<212> TYPE: PRT
<213> ORGANISM: Saccharomyces cerevisiae

<400> SEQUENCE: 6

Tyr Val Ser Gly Arg Val His Gly Glu Glu Asp Pro Thr Lys Lys
1               5                   10                  15

<210> SEQ ID NO 7
<211> LENGTH: 14
<212> TYPE: PRT
<213> ORGANISM: Saccharomyces cerevisiae

<400> SEQUENCE: 7

Lys Ala Asp Lys Val Ala Gly Lys Val Gln Pro Glu Asp Asn
1               5                   10

<210> SEQ ID NO 8
<211> LENGTH: 20
<212> TYPE: PRT
<213> ORGANISM: Saccharomyces cerevisiae

<400> SEQUENCE: 8

Lys Ala Ser Glu Ala Leu Lys Pro Asp Ser Gln Lys Ser Tyr Ala Glu
1               5                   10                  15

Gln Gly Lys Glu
            20

<210> SEQ ID NO 9
<211> LENGTH: 19
<212> TYPE: PRT
<213> ORGANISM: Saccharomyces cerevisiae

<400> SEQUENCE: 9

Asp Ala Val Glu Tyr Val Ser Gly Arg Val His Gly Glu Glu Asp Pro
1               5                   10                  15

Thr Lys Lys

<210> SEQ ID NO 10
<211> LENGTH: 24
<212> TYPE: PRT
<213> ORGANISM: Saccharomyces cerevisiae

<400> SEQUENCE: 10

Lys Ala Asp Lys Val Ala Gly Lys Val Gln Pro Glu Asp Asn Lys Gly
1               5                   10                  15

Val Phe Gln Gly Val His Asp Ser
            20

<210> SEQ ID NO 11
<211> LENGTH: 31
<212> TYPE: PRT
<213> ORGANISM: Saccharomyces cerevisiae

<400> SEQUENCE: 11

-continued

Lys Gly Val Phe Gln Gly Val His Asp Ser Ala Glu Lys Gly Lys Asp
1               5                   10                  15

Asn Ala Glu Gly Gln Gly Glu Ser Leu Ala Asp Gln Ala Arg Asp
            20                  25                  30

<210> SEQ ID NO 12
<211> LENGTH: 7
<212> TYPE: PRT
<213> ORGANISM: Saccharomyces cerevisiae

<400> SEQUENCE: 12

Lys Arg Val Phe Ile Arg Val
1               5

<210> SEQ ID NO 13
<211> LENGTH: 16
<212> TYPE: PRT
<213> ORGANISM: Saccharomyces cerevisiae

<400> SEQUENCE: 13

Asp Lys Ile Ser His Val Ser Thr Gly Gly Gly Ala Ser Leu Glu Leu
1               5                   10                  15

<210> SEQ ID NO 14
<211> LENGTH: 26
<212> TYPE: PRT
<213> ORGANISM: Saccharomyces cerevisiae

<400> SEQUENCE: 14

Glu Val Val Lys Ser Ser Ala Ala Gly Asn Thr Val Ile Ile Gly Gly
1               5                   10                  15

Gly Asp Thr Ala Thr Val Ala Lys Lys Tyr
            20                  25

<210> SEQ ID NO 15
<211> LENGTH: 23
<212> TYPE: PRT
<213> ORGANISM: Saccharomyces cerevisiae

<400> SEQUENCE: 15

Lys Ser Ser Ala Ala Gly Asn Thr Val Ile Ile Gly Gly Gly Asp Thr
1               5                   10                  15

Ala Thr Val Ala Lys Lys Tyr
            20

<210> SEQ ID NO 16
<211> LENGTH: 11
<212> TYPE: PRT
<213> ORGANISM: Saccharomyces cerevisiae

<400> SEQUENCE: 16

Arg Ile Val Ala Ala Leu Pro Thr Ile Lys Tyr
1               5                   10

<210> SEQ ID NO 17
<211> LENGTH: 11
<212> TYPE: PRT
<213> ORGANISM: Saccharomyces cerevisiae

<400> SEQUENCE: 17

Ala Gly Glu Asn Phe His His Gly Asp Lys Leu
1               5                   10

<210> SEQ ID NO 18

```
<211> LENGTH: 12
<212> TYPE: PRT
<213> ORGANISM: Saccharomyces cerevisiae

<400> SEQUENCE: 18

Phe Ala Gly Glu Asn Phe His His Gly Asp Lys Leu
1               5                   10

<210> SEQ ID NO 19
<211> LENGTH: 16
<212> TYPE: PRT
<213> ORGANISM: Saccharomyces cerevisiae

<400> SEQUENCE: 19

Tyr Ala Arg Ser Val Tyr Asp Ser Arg Gly Asn Pro Thr Val Glu Val
1               5                   10                  15

<210> SEQ ID NO 20
<211> LENGTH: 18
<212> TYPE: PRT
<213> ORGANISM: Saccharomyces cerevisiae

<400> SEQUENCE: 20

Asp Pro Glu Ala Ala Ala Ala Gly Ala Ala Ala Val Ala Asn Gln Gly
1               5                   10                  15

Lys Lys

<210> SEQ ID NO 21
<211> LENGTH: 17
<212> TYPE: PRT
<213> ORGANISM: Saccharomyces cerevisiae

<400> SEQUENCE: 21

Val Ser Leu Ala Ala Ser Arg Ala Ala Ala Ala Glu Lys Asn Val Pro
1               5                   10                  15

Leu

<210> SEQ ID NO 22
<211> LENGTH: 13
<212> TYPE: PRT
<213> ORGANISM: Saccharomyces cerevisiae

<400> SEQUENCE: 22

Arg Ala Ile Gln Thr Ala Asn Ile Ala Leu Glu Lys Ala
1               5                   10

<210> SEQ ID NO 23
<211> LENGTH: 21
<212> TYPE: PRT
<213> ORGANISM: Saccharomyces cerevisiae

<400> SEQUENCE: 23

Tyr Tyr Leu Asp Pro Glu Ala Ala Ala Gly Ala Ala Ala Val Ala
1               5                   10                  15

Asn Gln Gly Lys Lys
                20

<210> SEQ ID NO 24
<211> LENGTH: 14
<212> TYPE: PRT
<213> ORGANISM: Saccharomyces cerevisiae

<400> SEQUENCE: 24

Lys Ala Gly Val Val Lys Gly Lys Thr Leu Leu Glu Ala Ile
```

```
                1               5              10
```

<210> SEQ ID NO 25
<211> LENGTH: 14
<212> TYPE: PRT
<213> ORGANISM: Saccharomyces cerevisiae

<400> SEQUENCE: 25

```
Tyr Lys Ile Gly Gly Ile Gly Thr Val Pro Val Gly Arg Val
1               5                  10
```

<210> SEQ ID NO 26
<211> LENGTH: 19
<212> TYPE: PRT
<213> ORGANISM: Saccharomyces cerevisiae

<400> SEQUENCE: 26

```
Val Gln Ala Val Ala Val Leu Lys Gly Asp Ala Gly Val Ser Gly Val
1               5                  10                  15

Val Lys Phe
```

<210> SEQ ID NO 27
<211> LENGTH: 16
<212> TYPE: PRT
<213> ORGANISM: Saccharomyces cerevisiae

<400> SEQUENCE: 27

```
Ser Lys Asn Leu Tyr Ser Asn Lys Arg Leu Leu Thr Ser Thr Asn Thr
1               5                  10                  15
```

<210> SEQ ID NO 28
<211> LENGTH: 12
<212> TYPE: PRT
<213> ORGANISM: Saccharomyces cerevisiae

<400> SEQUENCE: 28

```
Arg Arg Val Leu Leu Ser Ala Pro Leu Ser Lys Glu
1               5                  10
```

<210> SEQ ID NO 29
<211> LENGTH: 16
<212> TYPE: PRT
<213> ORGANISM: Saccharomyces cerevisiae

<400> SEQUENCE: 29

```
Lys Asn Ala Lys Val Leu Glu Glu Asp Ala Pro Gly Tyr Lys Arg Glu
1               5                  10                  15
```